United States Patent
Vinet et al.

(10) Patent No.: US 7,442,823 B2
(45) Date of Patent: Oct. 28, 2008

(54) SILANYL-N-ALKANAL COMPOUNDS, METHOD FOR PRODUCTION AND USE THEREOF

(75) Inventors: Françoise Vinet, Grenoble (FR); Gérard Lanneau, Teyran (FR); Michel Granier, Teyran (FR); Franck Martin, Montpellier (FR)

(73) Assignees: Commissariat a l'Energie Atomique, Paris (FR); Centre National de la Recherche, Paris (FR); Universite de Montpellier 2, Montpellier Cedex (FR)

( * ) Notice: Subject to any disclaimer, the term of this patent is extended or adjusted under 35 U.S.C. 154(b) by 92 days.

(21) Appl. No.: 10/554,742

(22) PCT Filed: Apr. 28, 2004

(86) PCT No.: PCT/FR2004/001030

§ 371 (c)(1),
(2), (4) Date: Oct. 17, 2006

(87) PCT Pub. No.: WO2004/099219

PCT Pub. Date: Nov. 18, 2004

(65) Prior Publication Data

US 2007/0032672 A1    Feb. 8, 2007

(30) Foreign Application Priority Data

Apr. 30, 2003    (FR) .................................. 03 05391

(51) Int. Cl.
| | | |
|---|---|---|
| *C07F 7/04* | (2006.01) |
| *C07F 7/08* | (2006.01) |
| *C08F 290/14* | (2006.01) |
| *C08G 63/48* | (2006.01) |
| *C08G 63/91* | (2006.01) |
| *C12M 1/00* | (2006.01) |
| *C12M 3/00* | (2006.01) |
| *C12M 1/34* | (2006.01) |

(52) U.S. Cl. ...................... 556/436; 525/50; 435/285.1; 435/287.1

(58) Field of Classification Search ................. 556/436; 525/50; 435/285.1, 287.1
See application file for complete search history.

(56) References Cited

U.S. PATENT DOCUMENTS

2004/0039116 A1 * 2/2004 Vinet et al. ................. 525/54.1

FOREIGN PATENT DOCUMENTS

WO    WO 02/051856 A2    7/2002

OTHER PUBLICATIONS

Maskos, U., et al., "Oligonucleotide hybridizations on glass supports: a novel linker for oligonucleotide synthesis and hybridization properties of oligonucleotides synthesized in situ", *Nucleic Acids Research*, 20:7, 1992, 1679-1684.
Chrisey, L., et al., "Covalent attachment of synthetic DNA to self-assembled monolayer films", *Nucleic Acids Research*, 24:15, 1996, 3031-3039.
Database Registry, XP002273087.

* cited by examiner

*Primary Examiner*—Yvonne Eyler
*Assistant Examiner*—Jennifer Y Cho
(74) *Attorney, Agent, or Firm*—Rothwell, Figg, Ernst & Manbeck, P.C.

(57) ABSTRACT

The invention relates to ω-silanyl n-alkanal compounds, method for production and use thereof in the fuctionalization of solid supports, solid supports functionalized by the compounds and the use of solid supports thus functionalized for the immobilization and/or synthesis of biological molecules of interest.

10 Claims, 1 Drawing Sheet

SILANYL-N-ALKANAL COMPOUNDS, METHOD FOR PRODUCTION AND USE THEREOF

CROSS-REFERENCE TO RELATED APPLICATION

This application is a National Phase of International Application Serial No. PCT/FR2004/001030, filed Apr. 28, 2004.

BACKGROUND OF THE INVENTION

1. Field of the Invention

The present invention relates to ω-silanyl-n-alkanal compounds, to their process of preparation, to their use for the functionalization of solid supports, to the solid supports functionalized by these compounds and to the use of the solid supports thus functionalized for immobilization and/or synthesis of advantageous biological molecules.

2. Description of the Background Art

In order to carry out chemical syntheses or to immobilize advantageous biological molecules, such as nucleic acids, proteins or cell ligands, at the surface of a solid support (biochips), it is first of all necessary to graft, to the surface, coupling agents which will provide for the attachment of the organic molecules to the support.

The most commonly mentioned limitations in the preparation and the use of biochips and in particular of DNA biochips are the accessibility of the linking functional groups and the loss of selectivity due in particular to a change in the organic or inorganic interface, whether this is at the time of hybridization or else during the various rinsing stages, optionally during the recycling of the microsupport.

The synthetic scheme for the grafting of the molecules of oligonucleotides to the solid support presupposes the pretreatment of the surfaces (generally oxides or metals) with a coupling agent comprising a functional ending which will become arranged at the surface of the material.

Self-Assembled Monolayers (SAMs) are defined as an assemblage of molecules in which the molecules are arranged, which arrangement is due to interactions between the chains of the molecules, giving rise to a stable, monomolecular and well-ordered anisotropic film (A. Ulman, Chem. Rev., 1996, 96, 1533-1554). These self-assembled monolayers, which can be obtained reproducibly (J. B. Brozska et al., Langmuir, 1994, 10, 4367-4373), have the distinguishing feature for forming a dense and homogeneous film which is resistant to chemical treatments (acidic or basic chemical treatments). They are generally obtained from thiols, carboxylic acids or organosilicon compounds (also referred to as organofunctional silanes).

Organofunctional silanes are compounds which are particularly well suited to modifying surfaces of siliceous substrates. For example, they are used industrially as adhesion promoters (or coupling agents) by creating a molecular bridge between organic polymers and the oxide, resulting in composite materials.

Various organosilicon compounds have thus already been used as coupling agents for the functionalization of solid supports (L. A. Chrisey et al., Nucleic Acids Research, 1996, 24, 15, 3031-3039, U. Maskos et al., Nucleic Acids Research, 1992, 20, 7, 1679-1684) for the purpose of immobilizing or synthesizing in situ oligonucleotides. However, the organosilicon coupling agents used in these studies form nonhomogeneous films which show very little resistance to subsequent chemical treatments for the synthesis or immobilization of oligonucleotides. Furthermore, the formation of the films with these coupling agents is not reproducible.

The coupling agent properties of a silane depend on the nature of the organic R group but they depend in particular on the method of attachment to the surface via X functional groups. Thus, polyfunctional silanes of RSiX3 and R2SiX2 type, that is to say comprising three or two linking functional groups, not only hang on to the surface of the solid support but can also react with one another to form a crosslinked layer. In contrast, monofunctional silanes of R3SiX type, that is to say comprising only a single linking functional group, only get to hang on individually to the substrate.

The organosilanes RSiX3 and R3SiX have been the most widely studied in the literature, both from the academic viewpoint and from the industrial viewpoint, the first organosilanes because they result in the formation of a tridimensional network and the second organosilanes because they make it possible to determine the number of silanol sites present at the surface. The functional groups generally studied are the Si—Cl, Si—OMe and Si—OEt bonds and a classic example of surface modification with a trichlorosilane is given in Scheme A below:

SCHEME A

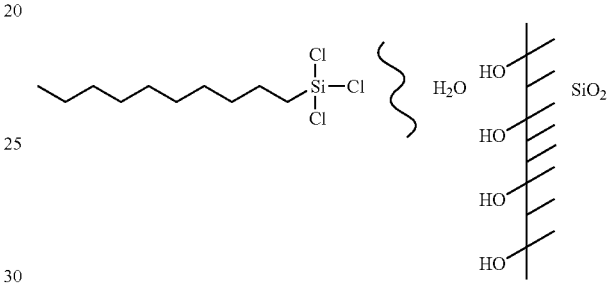

Stage 1

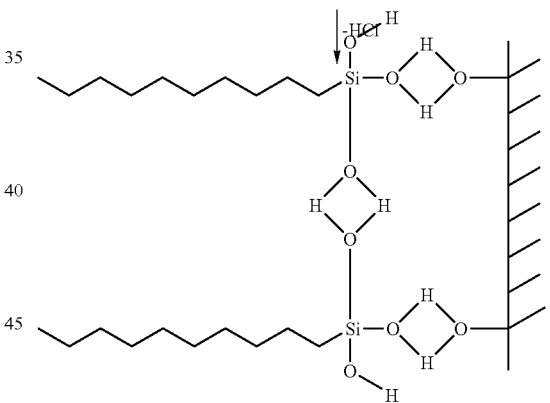

Stage 2

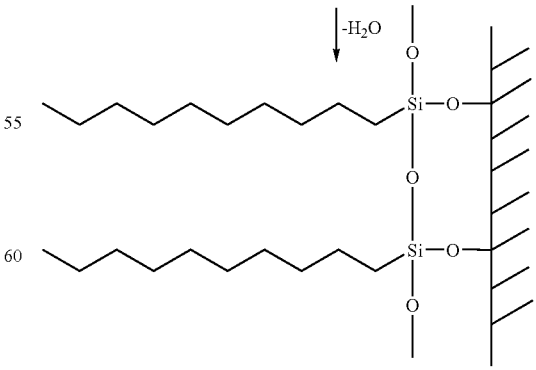

Stage 3

However, the use of these trichlorosilanes requires an additional stage, after grafting to the surface, of activation of the free bond in order to make possible the reaction with an amino group ($NH_2$) of a biological molecule. By way of example, when the grafted silane comprises an end epoxide functional group, the latter subsequently has to be activated according to a process employing two stages (a stage of opening the epoxide ring by hydrolysis, followed by an oxidation stage) in order to result in the corresponding reactive aldehyde functional group.

However, it is not always acceptable from an industrial viewpoint to carry out additional stages of activation of the end functional groups of the silanes in order to make possible the subsequent covalent attachment of biological molecules carrying a complementary functional group and to do so can have negative consequences with regard to the quality of the support finally obtained (loss of selectivity due in particular to a change in the organic/inorganic interface, poor distribution of the linking functional groups, and the like).

SUMMARY OF THE INVENTION

It is thus in order to overcome all these problems that the Inventors have developed that which forms the subject matter of the invention.

This is because the Inventors have set themselves the target of improving the attachment qualities of the surfaces currently used for carrying out the immobilization of advantageous biological molecules and their hold over time by controlling the linking functional groups and have developed novel compounds of silane type which meet this objective.

A subject matter of the present invention is thus ω-silanyl-n-alkanal compounds, characterized in that they correspond to the following formula (I):

$$CH(O)-C_nH_{2n}-SiH_3 \quad \text{(I)}$$

in which n represents a integer between 7 and 20 inclusive and preferably between 11 and 18 inclusive.

DETAILED DESCRIPTION OF THE INVENTION

Figure 1:
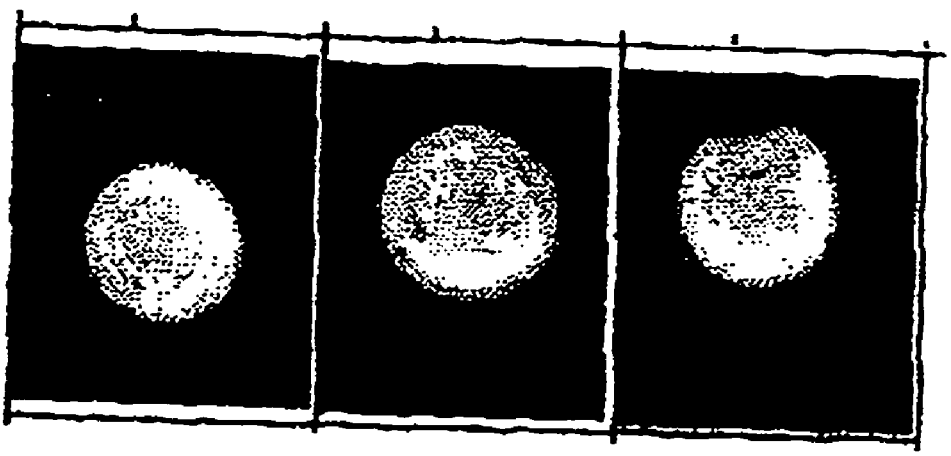
FIG. 1 is a fluorescence picture showing a hybridized target in accordance with the present invention.

These compounds are characterized in that they comprise an end aldehyde functional group which makes possible the direct grafting of any chemical or biological molecule comprising an end amine functional group, in contrast to all the compounds of silane type currently available, which require either a stage of modification (of activation) of the end chemical functional group of the silane after the stage of grafting to the surface of a support or the presence of an intermediate molecule, such as glutaraldehyde, for example, in order to make possible the grafting. Furthermore, the synthesis of these compounds requires specific conditions which are expanded upon below and which make it possible to retain the integrity of the aldehyde functional group.

Moreover, the Inventors have demonstrated that the compounds of formula (I) in accordance with the invention make it possible to functionalize the surface of solid supports comprising hydroxyl functional groups, this being achieved in a single stage, and result in the formation of self-assembled monolayers having a maximum density, in contrast to the SAMs formed from the known organosilanes of the prior art, such as, for example, the compounds of formula R—(CH3)2Si—X generally used.

This is because, if the steric hindrance of various silanes is compared, the presence of hydrogen atoms bonded to silicon results in the minimum space possible between the two silane chains, as may be seen in Scheme B below:

SCHEME B

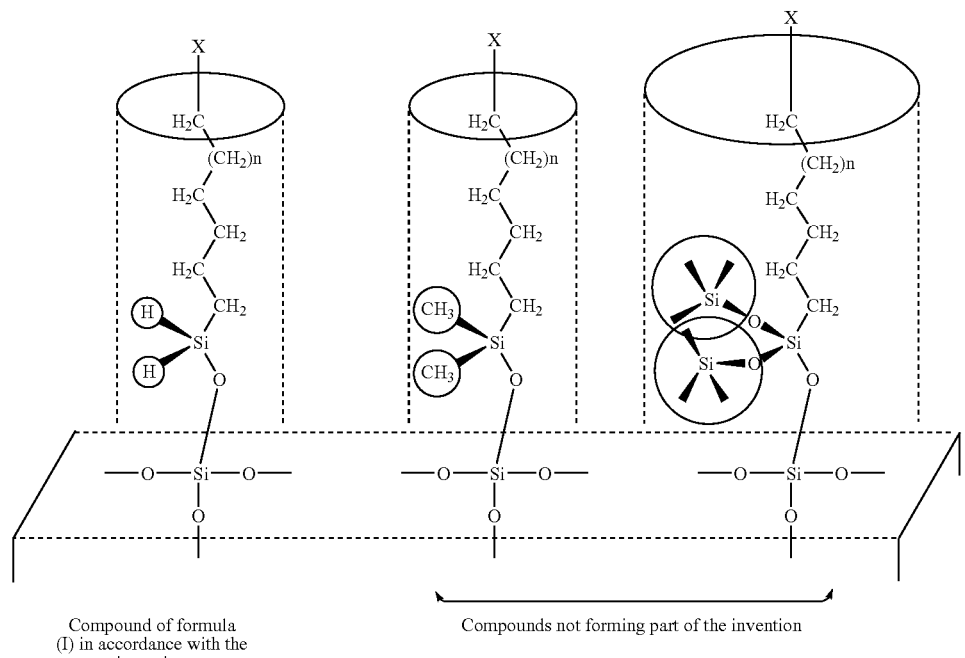

Compound of formula (I) in accordance with the invention

Compounds not forming part of the invention

Mention may in particular be made, among the compounds of formula (I) in accordance with the invention, of 8-silanyloctanal, 9-silanylnonanal, 10-silanyldecanal, 11-silanylundecanal, 12-silanyldodecanal, 13-silanyltridecanal, 14-silanyltetradecanal, 15-silanylpentadecanal, 16-silanylhexadecanal, 17-silanylheptadecanal, 18-silanyloctadecanal, 19-silanylnonadecanal and 20-silanyldodecanal; 11-silanylundecanal and 18-silanyloctadecanal being particularly preferred.

Another subject matter of the invention is the process for the preparation of the compounds of formula (I) as defined above, characterized in that:

(i) in a first stage, a compound of following formula (II):

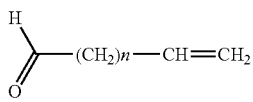

(II)

in which n is a number between 7 and 20 inclusive, is reacted in solution in an alcoholic solvent with ethyl orthoformate, at reflux and in the presence of a catalyst, in order to obtain a compound of following formula (III):

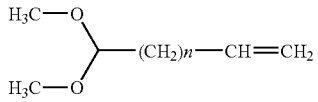

(III)

in which n has the same meaning as that indicated above for the compound of formula (II);

ii) in a second stage, the compound of formula (III) obtained in the first stage is reacted in solution in triethoxysilane in the presence of a catalyst, in order to obtain a compound of following formula (IV):

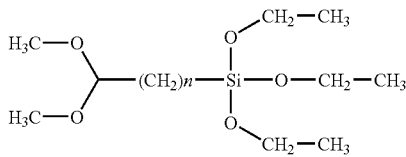

(IV)

in which n has the same meaning as that indicated above for the compound of formula (III);

iii) in a third stage, only the ethoxy groups carried by the compound of formula (IV) above are reduced in solution in an anhydrous solvent and in the presence of a mild reducing agent, in order to obtain a compound of following formula (V):

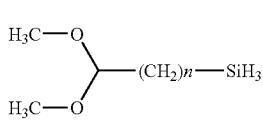

(V)

in which n has the same meaning as that indicated above for the compound of formula (IV);

iv) then, in a fourth stage, the compound of formula (V) above is oxidized in solution in an organic solvent and in the presence of an oxidizing agent, in order to obtain the corresponding compound of formula (I).

According to the invention, the term ""mild" reducing agent" is understood to mean any reducing agent capable of reducing the ethoxy groups carried by the silicon atom without, however, reducing the methoxy groups present in the compound of formula (IV). It is the judicious choice of this specific reducing agent which makes possible the synthesis of the compounds of formula (I) which directly comprise an end aldehyde functional group. This is because some weakly reducing agents, such as sodium borohydride, are not capable of reducing the ethoxy groups carried by the compounds of formula (IV), whereas more strongly reducing agents, such as lithium trihydroaluminate, result not only in the reduction of the ethoxy groups but also in that of the methoxy groups of the compounds of formula (IV), thus precluding the subsequent formation of the aldehyde functional group during the fourth stage.

At each stage of this process, the intermediate compounds of formulae (II) to (V) and the final compound of formula (I) at the end of the synthesis are preferably washed, isolated and purified according to methods conventionally used for this purpose.

The organic solvents used during the first stage are preferably chosen from lower alcohols, such as methanol and ethanol. The reaction is preferably carried out at the reflux temperature of the solvent and the duration of the reaction is generally between 8 and 16 hours. The catalyst used during the first stage is preferably para-toluenesulfonic acid used in a catalytic amount, that is to say at approximately 0.5%.

The catalyst used during the second stage is preferably chosen from homogeneous phase catalysts based on transition metals; the Karstedt catalyst being particularly preferred.

During the third stage, the anhydrous solvent is preferably chosen from ethers and cyclic ethers; ethyl ether being particularly preferred. The "mild" reducing agent is preferably lithium tetrahydroaluminate.

The organic solvent used during the fourth stage is preferably chosen from chlorinated solvents; chloroform being particularly preferred. The oxidizing agent is preferably chosen from strong carboxylic or inorganic acids; trifluoroacetic acid (TFA) being particularly preferred.

The compounds of formula (I) in accordance with the invention can be used to form a self-assembled monolayer arranged at the surface of a solid support.

Thus, another subject matter of the present invention is the use of at least one compound of formula (I) as described above to form, at the surface of a solid support comprising hydroxyl functional groups, an arranged self-assembled monolayer.

The use of the compounds of formula (I) makes it possible advantageously to modify the surface of solid supports with an arranged monolayer of maximum density, which corresponds to the definition of the SAMs given previously.

These SAMs can be prepared in a way conventional to a person skilled in the art by bringing at least one hydroxylated surface of a solid support into contact with a solution of at least one compound of formula (I) in accordance with the invention in an organic solvent, such as, for example, trichloroethylene, at a temperature of between 2 and 10° C. approximately for 12 to 24 hours approximately. The substrate is subsequently rinsed with various solvents, preferably and successively with trichloroethylene, ethanol, chloroform and pentane, and then dried, preferably with nitrogen.

These two characteristics, namely a minimum of chemical stages for the functionalization of the surface and the production of a self-assembled monolayer of maximum density, make it possible to eliminate the problems of reproducibility of the processes currently used.

Furthermore, the surfaces thus obtained directly exhibit a large number of aldehyde functional groups which make it possible to covalently immobilize advantageous biological molecules comprising a complementary amine functional group, this being the case without it being necessary to carry out a preliminary activation of the support. The compounds grafted to the support give rise to strong covalent bonds, of siloxane type, with the surface and develop strong cohesion between their alkyl chains, the result of a self-assembling of the molecules, which protects the siloxane bonds. In addition, the grafting is reproducible and the aldehyde functional group of the grafted compounds exhibits a high chemical reactivity.

The roughnesses of the surfaces, measured by atomic force microscopy (AFM), of the support, treated by thermal oxidation and after covalent coupling of the compounds of formula (I) in accordance with the invention, are respectively 0.8 Å and 2.3 Å, which indicates the deposition of a homogeneous layer. By way of example, the thickness of the layer, measured by ellipsometry, after grafting of a SAM with a compound of formula (I) in which n=11 is 19.9±2.6 Å (for a refractive index of 1.45), whereas the theoretical value for a C11 carbon chain orthogonal to the surface is 18.15 Å.

Furthermore, the byproduct of the grafting reaction of the compounds of formula (I) in accordance with the invention with the hydroxylated surface of a solid support is an evolution of hydrogen, which is easy to remove, in contrast to the anionic entities or to the proton compounds which are inherent in the processes of the prior art using chlorosilanes or alkoxysilanes. The grafting reaction results in the substitution of a single Si—H bond, that is to say that the compound of formula (I) in accordance with the invention behaves as a monofunctional organosilane. In the present case, activation of the Si—H bonds corresponds to the arrangement of the long alkyl chains in the vicinity of the surface, which can make possible the transitory formation of hypercoordinated silicon entities, of the $[R-SiH_4]^-$ or $[R-SiH_5]^{2-}$ type, which are known to be more reactive than tetrahedral entities.

In fact, attenuated total reflectance infrared (ATR-IR) spectroscopic analysis makes it possible to identify the presence at the surface of $RSiH_2$—O— entities alone, clearly showing that only monoattachment has occurred.

Another subject matter of the present invention is a solid support, at least one surface of which is modified by an arranged self-assembled monolayer, characterized in that said monolayer comprises a network of at least one compound of formula (I) as defined above.

Within the meaning of the present invention, the term "network" is understood to mean an assembly of molecules in which the molecules are arranged and in which the chains to the molecules interact with one another via noncovalent bonds (Van der Waals forces, for example).

Any solid support comprising at least one hydrated surface can be functionalized by the compounds of formula (I) in accordance with the invention. Preferably, said solid support is such that its surface exhibits, before being modified, hydroxyl groups. It is advantageously selected from the group consisting of glasses, ceramics of oxide type and plastics.

It is clearly understood that said monolayer, in addition to compounds of general formula (I) according to the present invention, can also comprise any other type of compound capable of being grafted to the solid support (production of a "mixed" monolayer), which makes it possible to reduce the density of the compounds of formula (I) on the support, when such an effect is desired.

The solid supports, the surface of which is modified by an arranged self-assembled monolayer according to the present invention, can advantageously be used as supports for the synthesis or immobilization by the covalent route of advantageous biological or chemical molecules comprising an amine functional group. Mention may be made, among such molecules, for example, of nucleic acids, such as DNA and oligonucleotides, proteins, cell ligands, therapeutic target molecules and combinatorial chemistry ligands.

Thus, another subject matter of the present invention is the use of a solid support as described above for the synthesis or the immobilization of molecules by covalent bonding (formation of an amide bond).

Another subject matter of the present invention is a process for the synthesis of molecules on a solid support as described above, characterized in that said molecules are composed of a sequence of repeat units and in that said process comprises successive stages of grafting to said repeat units, the first repeat unit grafted carrying an amine functional group which is reactive with regard to the aldehyde functional groups of the compounds of formula (I) in accordance with the invention present on the solid support.

A subject matter of the present invention is additionally a process for the immobilization of biomolecules on a solid support as described above, characterized in that it comprises a stage of grafting said biomolecules, which carry amine functional groups which are reactive with regard to the aldehyde functional groups of the compounds of formula (I) in accordance with the invention, to said solid support.

Finally, another subject matter of the invention is the solid supports as described above on which biological or chemical molecules are covalently immobilized via an amide functional group (nucleic acid chips, protein chips, cell ligand chips, and the like).

Figure 2:
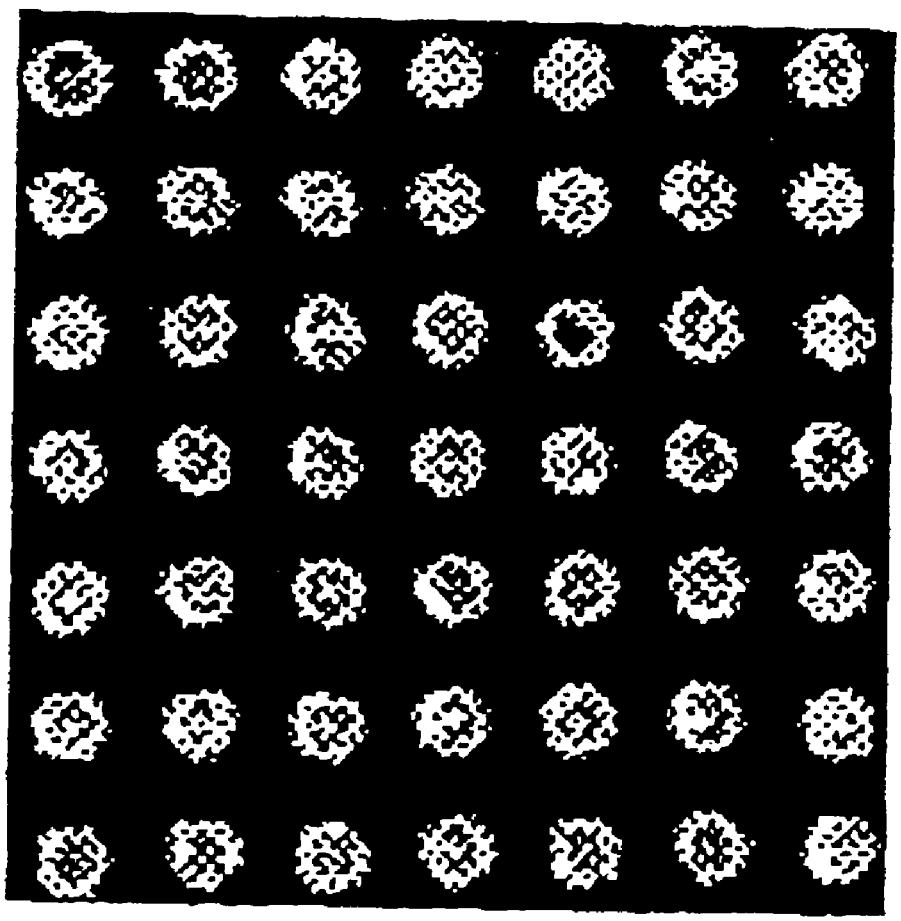
FIG. 2 is a fluorescence picture showing a hybridized target in accordance with another embodiment.

In addition to the preceding arrangements, the invention also comprises other arrangements which will emerge from the description which will follow, which refers to an example of the preparation of a compound of formula (I) in accordance with the invention, to an example of the functionalization of the surface of a solid support using a compound of formula (I), to an example of the use of a support functionalized by a compound of formula (I) for the manufacture of a DNA chip, and to the appended FIGS. 1 and 2, in which:

the picture of the fluorescence obtained on an epifluorescence microscope after grafting 11-silanylundecanal to the surface of a siliceous support, grafting an oligonucleotide (deposited manually) and hybridizing with a complementary target is represented in FIG. 1;

the picture of the fluorescence obtained on a scanner after grafting 11-silanylundecanal to the surface of a siliceous support, grafting an oligonucleotide (deposited using an automated device) and hybridizing with a complementary target is represented in FIG. 2.

It should be clearly understood, however, that these examples are given solely by way of illustration of the subject matter of the invention and do not constitute in any way a limitation thereof.

EXAMPLE 1

Preparation of 11-Silanyludecalal (10)

1) First Stage: Synthesis of 11,11-dimethoxyundec-1-ene (7)

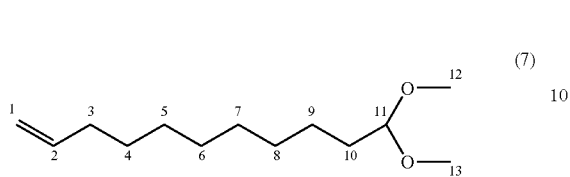

37.78 g of ethyl orthoformate (13.09 ml, 356 mmol, 2 eq.) and 1.691 g of para-toluenesulfonic acid (catalytic amount: 8.9 mmol, 0.051 eq.) are added to a solution of 30.05 g of 97% undecenal (37.10 ml, 173 mmol) dissolved in 500 ml of methanol. The reaction takes place over 12 hours and at reflux of the methanol. After addition of 500 ml of dichloromethane, the reaction mixture is washed successively with a 1% sodium carbonate solution (two times) and with a saturated sodium chloride solution, dried over anhydrous magnesium sulfate and then concentrated to give 36.39 g of a brown liquid with a yield of 97%.

The NMR analysis of the product obtained, in accordance with that of the product expected, was as follows:

$\delta_H$ (200 MHz, CDCl$_3$): 1.31 (12H, m, H$^{4-9}$), 1.59 (2H, m, H$^{10}$), 2.06 (2H, m, H$^3$), 3.21 (6H, s, H$^{12+13}$), 4.38 (1H, t, H$^{11}$, $^3J_{H-H}$ 5.7 Hz), 4.98 (2H, m, H$^1$), 5.81 (1H, m, H$^2$), $\delta_c$ (200 MHz, CDCl$_3$): 24.97, 29.30, 29.48, 29.76, 29.84, 29.87, 32.87, 34.18, 52.91 (C$^{12+13}$), 104.94 (C$^{11}$), 114.48 (C$^1$), 139.54 (C$^2$), m/z (NBA): 213 [M-H]$^+$.

2) Second Stage: Synthesis of (11,11-dimethoxyun-decyl)triethoxysilane (8)

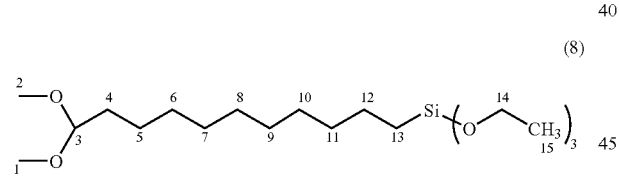

36.39 g of 11,11-dimethoxyundec-1-ene (7) obtained above in the first stage (170 mmol) are dissolved in 31.025 g of 97% triethoxysilane (34.86 ml, 183 mmol, 1.08 eq.). Subsequently, 0.424 g (0.45 mmol, 0.0026 eq.) of Karstedt catalyst is added very slowly. After stirring at ambient temperature for 3 hours, the crude reaction product is purified by distillation to give 41.88 g of a colorless liquid (yield of 65%) melting at a temperature of 115°-120° C. (at a pressure of 10$^{-2}$ mm of mercury).

The NMR analysis of the product obtained, in accordance with that of the product expected, was as follows:

$\delta_H$ (200 MHz, CDCl$_3$): 0.59 (2H, m, H$^{13}$), 1.19 (9H, t, H$^{15}$, $^3J_{H-H}$ 7 Hz), 1.22 (16H, m, H$^{5-12}$), 1.53 (2H, m, H$^4$), 3.27 (6H, s, H$^{1+2}$), 3.76 (6H, q, H$^{14}$, $^3J_{H-H}$ 7 Hz), 4.32 (1H, t, H$^3$, $^3J_{H-H}$ 5.7 Hz), $\delta_c$ (200 MHz, CDCl$_3$): 10.70 (C$^{13}$), 18.60 (C$^{15}$), 23.08, 24.93, 29.56, 29.82, 29.88, 32.80, 33.49, 33.49, 52.79 (C$^{1+2}$), 58.56 (C$^{14}$), 104.86 (C$^3$), $\delta_{si}$ (200 MHz, CDCl$_3$): -44.23, m/z (NBA): 377 [M-H]$^+$.

3) Third Stage: Synthesis of (11,11-dimethoxyundecyl)silane (9)

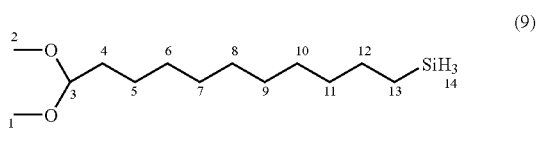

A solution of 21.016 g of the compound (8) obtained above in the preceding stage (55.6 mmol) dissolved in 500 ml of anhydrous ether is slowly added to a solution of 4.22 g of lithium tetrahydroaluminate (111 mmol, 2 eq.) mixed with 500 ml of anhydrous ethyl ether and cooled to 0° C. The reduction reaction takes place over 48 hours, at ambient temperature and under argon. The reaction mixture is filtered through celite, the filtrate is then evaporated and the residue is taken up in dichloromethane. Subsequently, the organic phase is washed successively with a 1N hydrochloric acid solution (two times) and with a saturated sodium chloride solution, dried over anhydrous magnesium sulfate and then concentrated. The crude reaction product is purified by distillation to give 16.147 g of a colorless liquid (yield 60%) melting at a temperature of 60°-65° C. (at a pressure of 10$^{-2}$ mm of mercury).

The NMR and IR analyses of the product obtained, in accordance with those of the expected product, were as follows:

NMR: $\delta$HH (200 MHz, CDCl3): 0.78 (2H, m, H13), 1.30 (16H, m, H5-12), 1.64 (2H, m, H4), 3.36 (6H, s, H1+2), 3.51 (3H, t, H14, 3JH-H 3.9 Hz), 4.39 (1H, t, H3, 3JH-H 5.7 Hz), $\delta$C (200 MHz, CDCl3): 6.28 (C13), 24.98, 26.73, 29.62, 29.85, 29.92, 29.98, 32.83, 32.86, 52.81 (C1+2), 104.87 (C3), $\delta$Si (200 MHz, CDCl3): -58.93;

IR: 1056.7 and 1125.7 (CO), 2149.2 (SiH3), 2854 (s CH2), 2924 (as CH$_2$), m/z (NBA): 245 [M-H]$^+$.

4) Fourth Stage: Synthesis of 11-silanylundecanal (10)

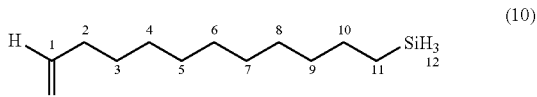

14.8 g of trifluoroacetic acid (130 mmol, 10 ml) are added to a solution of 13.106 g of (11,11-dimethoxyundecyl)silane (9) obtained above in the preceding stage (53.3 mmol) dissolved in 50 ml of chloroform. The oxidation reaction takes place over 12 hours and at ambient temperature. The reaction mixture is subsequently evaporated and the residue is taken up in ether. The organic phase is then washed successively with a sodium carbonate solution (two times), with a deionized water solution (two times) and with a saturated sodium chloride solution, dried over anhydrous magnesium sulfate and then concentrated. The crude reaction product is purified by distillation to give 7.036 g of a colorless liquid (yield 66%) melting at a temperature of 60°-65° C. (at a pressure of 7.5×10$^-$1 mm of mercury).

The NMR and IR analyses of the product obtained, in accordance with those of the expected product, were as follows:

NMR: $\delta$H (200 MHz, CDCl3): 0.73 (2H, m, H1), 1.27 (16H, m, H4-10), 1.61 (2H, m, H3), 2.41 (2H, td, H2, 3JH-H1 3.9 Hz, 3JH-H1 7.4 Hz), 3.47 (3H, t, H12, 3JH-H 3.9 Hz), 9.75 (1H, t, H1, 3JH-H 1.9 Hz), δC (200 MHz, CDCl3): 6.30 (C11), 22.47, 26.73, 29.60, 29.63, 29.88, 29.94, 32.85, 32.87, 44.30 (C2), 203.33 (C1), δSi (200 MHz, CDCl3): −58.97; IR: 1728 (C=O), 2149 (SiH3), 2714 (CHO), 2854 (s CH2), 2924 (as CH2), m/z (NBA): 199 [M-H]+.

EXAMPLE 2

Preparation of a Solid Support Comprising a Surface Modified by a Self-Assembled Monolayer of Compounds of Formula (I)

In this example, the 11-silanylundecanal prepared above in example 1 is used as compound of formula (I).

A silicon substrate covered with a 5000 Å thermal oxide layer is hydroxylated in a 3.5 M sodium hydroxide solution for 2 hours.

The support is subsequently brought into the presence of a 10 mM solution of 11-silanylundecanal in trichloroethylene at a temperature of 4° C. for 24 hours. The support is subsequently rinsed successively with trichloroethylene, ethanol, chloroform and pentane and then dried with nitrogen.

A solid support in accordance with the invention comprising a surface modified by a self-assembled monolayer formed of 11-silanylundecanal is obtained. EXAMPLE 3

Preparation of a DNA Chip

In this example, the modified solid support prepared above in example 2 is used.

Samples of a solution of oligonucleotides with the following sequence: 3' ATG TCA CAT GCC AAA TAG 5' (SEQ ID No. 1), which are modified in the 5' position by an amine functional group, are deposited on the modified solid support of example 2, either manually, in a proportion of 1.5 µl, or using a piezoelectric ejection automated device sold under the name Nano-Plotter® by GeSiM (Germany), in a proportion of 1.5 µl, or using a piezoelectric ejection automated of 300 pl. The concentration of oligonucleotides in the solution used is 10 µm in a 0.3M Na2PO4 buffer.

After an incubation time of 24 hours, the substrates are hybridized with a solution of complementary targets with the following sequence: 3' TAG AGT GTA CGG TTT ATC 5' (SEQ ID NO: 2), with a concentration of 0.1 µM, which are labeled with a Cy3 fluorescent group.

The fluorescence signals, obtained on an epifluorescence microscope sold under the name by Olympus Inc. (USA) and on a scanner sold under the name GenePix® by Axon, are presented respectively in the appended FIGS. 1 and 2.

These results show that the supports modified by a self-assembled monolayer of compounds of formula (I) in accordance with the invention make it possible to carry out the immobilization of molecules comprising a complementary amine functional group.

What is claimed is:

1. An ω-silanyl-n-alkanal compound, characterized in that it corresponds to the following formula (I):

$$CH(O)-C_nH_{2n}-SiH_3 \quad (I)$$

in which n represents an integer between 7 and 20 inclusive.

2. The compound as claimed in claim 1, characterized in that n is between 11 and 18 inclusive.

3. The compound as claimed in claim 1, characterized in that it is chosen from 8-silanyloctanal, 9-silanylnonanal, 10-silanyldecanal, 11-silanylundecanal, 12-silanyldodecanal, 13-silanyltridecanal, 14-silanyltetradecanal, 15-silanylpentadecanal, 16-silanylhexadecanal, 17-silanylheptadecanal, 18-silanyloctadecanal, 19-silanylnonadecanal and 20-silanyldodecanal.

4. A process for the preparation of the compound of formula (I) as defined in claim 1, characterized in that:

(i) in a first stage, a compound of following formula (II):

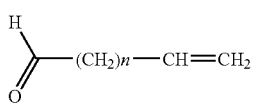
(II)

in which n is a number between 7 and 20 inclusive, is reacted in solution in an alcoholic solvent with ethyl orthoformate, at reflux and in the presence of a catalyst, in order to obtain a compound of following formula (III):

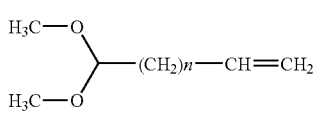
(III)

in which n has the same meaning as that indicated above for the compound of formula (II);

ii) in a second stage, the compound of formula (III) obtained in the first stage is reacted in solution in triethoxysilane in the presence of a catalyst, in order to obtain a compound of following formula (IV):

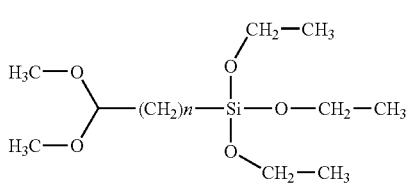
(IV)

in which n has the same meaning as that indicated above for the compound of formula (III);

iii) in a third stage, only the ethoxy groups carried by the compound of formula (IV) above are reduced in solution in an anhydrous solvent and in the presence of a mild reducing agent, in order to obtain a compound of following formula (V):

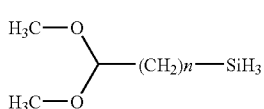
(V)

in which n has the same meaning as that indicated above for the compound of formula (IV);

iv) then, in a fourth stage, the compound of formula (V) above is oxidized in solution in an organic solvent and in the presence of an oxidizing agent, in order to obtain the corresponding compound of formula (I).

5. The process as claimed in claim 4, characterized in that the mild reducing agent used during the third stage is lithium tetrahydroaluminate.

6. A method of modifying a solid support surface comprising hydroxyl functional groups, said method comprising functionalizing said hydroxyl functional groups with at least one compound of formula (I) as defined in claim 1, to produce an arranged self-assembled monolayer.

7. A process for the preparation of the compound of formula (I) as defined in claim 2, characterized in that:

(i) in a first stage, a compound of following formula (II):

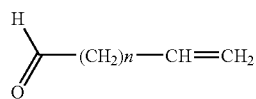
(II)

in which n is a number between 7 and 20 inclusive, is reacted in solution in an alcoholic solvent with ethyl orthoformate, at reflux and in the presence of a catalyst, in order to obtain a compound of following formula (III):

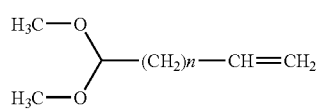
(III)

in which n has the same meaning as that indicated above for the compound of formula (II);

ii) in a second stage, the compound of formula (III) obtained in the first stage is reacted in solution in triethoxysilane in the presence of a catalyst, in order to obtain a compound of following formula (IV):

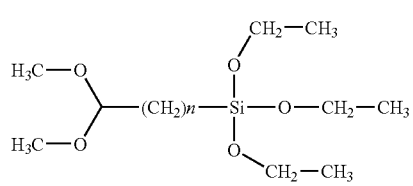
(IV)

in which n has the same meaning as that indicated above for the compound of formula (III);

iii) in a third stage, only the ethoxy groups carried by the compound of formula (IV) above are reduced in solution in an anhydrous solvent and in the presence of a mild reducing agent, in order to obtain a compound of following formula (V):

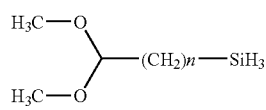
(V)

in which n has the same meaning as that indicated above for the compound of formula (IV);

iv) then, in a fourth stage, the compound of formula (V) above is oxidized in solution in an organic solvent and in the presence of an oxidizing agent, in order to obtain the corresponding compound of formula (I).

8. A process for the preparation of the compound of formula (I) as defined in claim 3, characterized in that:

(i) in a first stage, a compound of following formula (II):

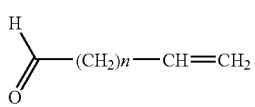
(II)

in which n is a number between 7 and 20 inclusive, is reacted in solution in an alcoholic solvent with ethyl orthoformate, at reflux and in the presence of a catalyst, in order to obtain a compound of following formula (III):

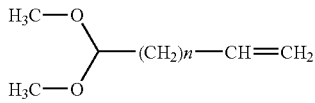
(III)

in which n has the same meaning as that indicated above for the compound of formula (II);

ii) in a second stage, the compound of formula (III) obtained in the first stage is reacted in solution in triethoxysilane in the presence of a catalyst, in order to obtain a compound of following formula (IV):

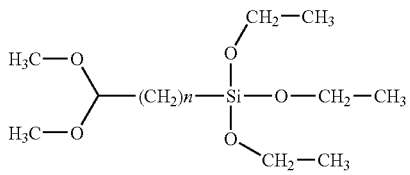
(IV)

in which n has the same meaning as that indicated above for the compound of formula (III);

iii) in a third stage, only the ethoxy groups carried by the compound of formula (IV) above are reduced in solution in an anhydrous solvent and in the presence of a mild reducing agent, in order to obtain a compound of following formula (V):

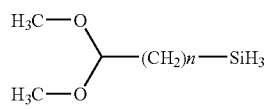
(V)

in which n has the same meaning as that indicated above for the compound of formula (IV);

iv) then, in a fourth stage, the compound of formula (V) above is oxidized in solution in an organic solvent and in the presence of an oxidizing agent, in order to obtain the corresponding compound of formula (I).

9. A method of modifying a solid support surface comprising hydroxyl functional groups, said method comprising functionalizing said hydroxyl functional groups with at least one compound of formula (I) as defined in claim 2, to produce an arranged self-assembled monolayer.

10. A method of modifying a solid support surface comprising hydroxyl functional groups, said method comprising functionalizing said hydroxyl functional groups with at least one compound of formula (I) as defined in claim 3, to produce an arranged self-assembled monolayer.

* * * * *

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Probe

<400> SEQUENCE: 1
gataaaccgt acactgta                                                 18

<210> SEQ ID NO 2
<211> LENGTH: 18
<212> TYPE: DNA
<213> ORGANISM: Artificial Sequence
<220> FEATURE:
<223> OTHER INFORMATION: Target

<400> SEQUENCE: 2
ctatttggca tgtgagat                                                 18
```